United States Patent
Botos et al.

(10) Patent No.: US 7,084,533 B2
(45) Date of Patent: Aug. 1, 2006

(54) DUAL-FUNCTION THREE-AXIS POSITIONING SYSTEM

(75) Inventors: Stephen J. Botos, Pittsburgh, PA (US); Brian P. O'Connor, Allison Park, PA (US)

(73) Assignee: Aerotech, inc., Pittsburgh, PA (US)

( * ) Notice: Subject to any disclaimer, the term of this patent is extended or adjusted under 35 U.S.C. 154(b) by 0 days.

(21) Appl. No.: 11/019,019

(22) Filed: Dec. 21, 2004

(65) Prior Publication Data

US 2005/0238452 A1    Oct. 27, 2005

Related U.S. Application Data

(63) Continuation-in-part of application No. 10/830,979, filed on Apr. 23, 2004.

(51) Int. Cl.
    *B23Q 17/00* (2006.01)
(52) U.S. Cl. .............................. 310/12; 74/826; 29/759
(58) Field of Classification Search ............ 219/67–69, 219/82, 84, 69.1, 69.11, 714, 759, 407.1, 219/407.05; 623/1.15, 901; 29/896.6; 74/826, 74/813 R, 813 L, 813 C; 310/12
See application file for complete search history.

(56) References Cited

U.S. PATENT DOCUMENTS

| | | | | |
|---|---|---|---|---|
| 2,338,060 A | * | 12/1943 | Redmer | 279/4.09 |
| 3,571,634 A | * | 3/1971 | Sato et al. | 310/54 |
| 5,346,345 A | * | 9/1994 | Jerzycke et al. | 409/235 |
| 5,368,425 A | * | 11/1994 | Mills et al. | 409/235 |
| 5,731,641 A | * | 3/1998 | Botos et al. | 310/12 |
| 5,759,192 A | * | 6/1998 | Saunders | 606/194 |
| 6,323,935 B1 | * | 11/2001 | Ebihara et al. | 355/53 |
| 6,356,219 B1 | * | 3/2002 | Weibel, IV et al. | 341/120 |
| 6,511,504 B1 | * | 1/2003 | Lau et al. | 623/1.15 |
| 6,588,081 B1 | * | 7/2003 | Botos et al. | 29/281.5 |
| 6,698,982 B1 | * | 3/2004 | Watanabe et al. | 409/168 |
| 6,905,292 B1 | * | 6/2005 | Schuon | 409/2 |
| 6,927,838 B1 | * | 8/2005 | Ono et al. | 355/72 |
| 7,038,334 B1 | * | 5/2006 | Botos et al. | 310/12 |

* cited by examiner

*Primary Examiner*—Karl Tamai
*Assistant Examiner*—Judson H. Jones
(74) *Attorney, Agent, or Firm*—The Webb Law Firm

(57) ABSTRACT

A dual-function, three-axis positioning system having a high precision z-theta state with a horizontal translation axis (z-axis) and a rotary axis (theta-axis) parallel with the translation axis and a second horizontal translation axis (x-axis) comprises parallel spaced apart linear translation states, a first carriage supported between the parallel translation stages, and a rotation stage carried by the carriage between the parallel translation stages. A removable or permanently fixed second carriage is mounted on or being part of the first carriage.

8 Claims, 3 Drawing Sheets

DUAL-FUNCTION THREE-AXIS POSITIONING SYSTEM

BACKGROUND OF THE INVENTION

This patent relates to a three-axis positioning system comprising a high precision z-theta stage and an x-stage mounted thereon. The three-axis positioning system has a horizontal translation axis (z-axis), a rotary axis (theta-axis) parallel with the horizontal translation axis, and a second horizontal translation axis (x-axis). The three-axis positioning system is especially designed for the laser machining of cylindrical and other types of components. It can also be used for the precision manufacture, say laser welding, cutting, and drilling of parts, such as cases for implantable pacemakers, stents, or many other types of discrete parts. The stents are manufactured from a tubular feedstock, such as stainless steel, nitinol, or plastic, and are provided with intricate circumferential patterns. Processes for machining the patterns out of the feedstock include laser machining in which a z-theta stage controlled by a CNC controller presents the feedstock to a laser beam for cutting away portions of the tubular feedstock. See U.S. Pat. No. 6,511,504 entitled "Expandable Stents and Method for Making Same" for a description of one stent manufacturing process.

SUMMARY OF THE INVENTION

Briefly, according to the present invention, the dual-function, three-axis positioning system comprises a high precision z-theta stage that has a horizontal translation axis (z-axis), a rotary axis (theta-axis) parallel with the translation axis, and a removable, or permanently fixed translation stage that has a second horizontal translation axis (x-axis) preferably perpendicular to the z-axis. The z-theta stage comprises a base plate having upper surfaces lying in a plane and parallel spaced apart linear translation stages each having parallel linear bearings with bearing surfaces mounted at a substantially equal distance from the planar surfaces of the base plate. Each linear translation stage has a brushless linear motor. A first carriage is supported between the parallel translation stages by the linear bearings. A rotation stage is housed in the first carriage between the parallel translation stages; the rotation stage comprises a brushless rotating motor having a shaft journaled with an axis parallel to the linear bearings. The first carriage and rotation stage have a vertical and a horizontal center of gravity. Each brushless linear motor is connected to the first carriage by applying translation forces in a horizontal plane intersecting the vertical center of gravity of the carriage. Removably mounted on, or permanently fixed over the first carriage is a second carriage. A brushless linear motor is connected between the first and second carriages for relative translation motion therebetween.

A linear position feedback device comprising a resolver, a laser interferometer, or an encoder may be associated with one or more of the brushless linear motors. A rotary feedback device comprising a resolver or encoder may be associated with the brushless rotating motor.

The high precision z-theta stage may have a pneumatic-actuated, workpiece-holding chuck or collet attached to the rotor.

The rotor is preferably hollow to permit a cylindrical workpiece and/or a fluid cooling jacket to be advanced therethrough or positioned therein.

Most preferably, auxiliary tooling is arranged to support brackets guiding, grasping, and feeding a workpiece along the axis of the rotor.

Preferably, the horizontal center of gravity of the carriage and rotary stage is located halfway between each linear motor.

Preferably, the first and second carriages are associated with linear motion guides, cross roller bearings, or air bearings.

Preferably, each linear motor is connected to a carriage at multiple locations spaced in the direction of linear translation.

BRIEF DESCRIPTION OF THE DRAWINGS

Further features and other objects and advantages will become clear from the following detailed description made with reference to the drawings in which.

DESCRIPTION OF THE PREFERRED EMBODIMENTS

Figure 1:
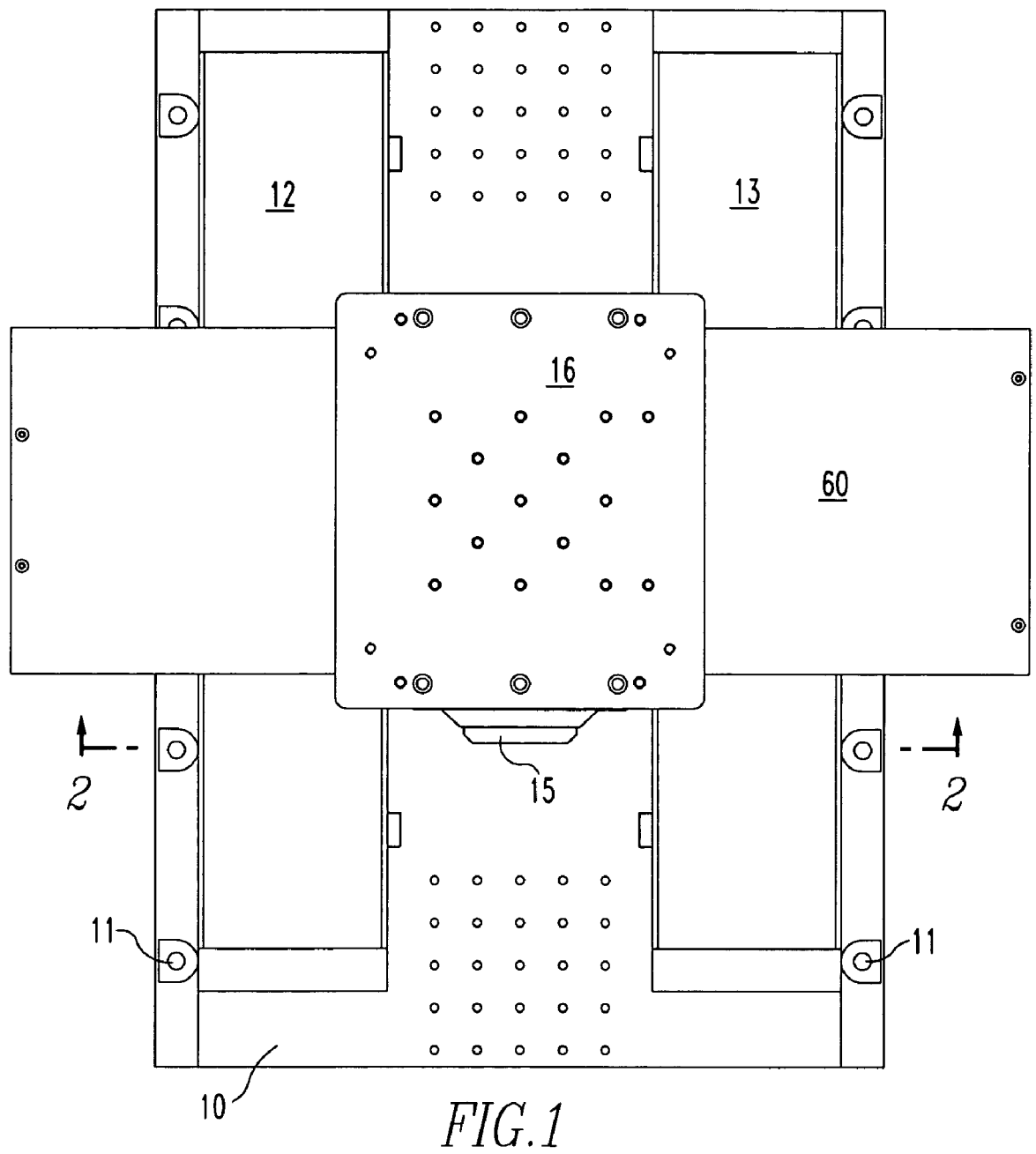
FIG. 1 is a plan view of the dual-function stage according to the present invention.

Referring to FIG. 1, there is shown a dual-function, three-axis positioning system which comprises a z-theta stage suitable for manufacture of precision parts, such as stents. The stage includes a base plate 10 which is provided with openings 11 to receive bolts for securing the stage to a foundation which is usually a large piece of granite, a casting, or a welded structure. The base plate 10 is fabricated from metal, steel, or aluminum, for example. Mounted to the base plate are two parallel linear motors 12 and 13. Mounted between the linear motors and carried by them is a first carriage 14 (see FIG. 2) which supports a rotary motor 15 having an axis parallel to the translation axes of the linear motors. Preferably, the z-axis is horizontal or substantially horizontal. The linear motors define the z-axis and the rotary motor the theta-axis of the z-theta stage. Removably mounted or permanently fixed to the first carriage 14 is a second carriage 16 which is part of an x-stage which defines the x-axis which is preferably perpendicular to the z-axis.

An essential feature of the present invention is that, if/or when the second carriage is removed, the linear motors 12, 13 are connected to the first carriage to apply translation forces to the first carriage 14 directed along the surface of a plane that includes the vertical center of gravity of the first carriage 14 or passes as close to the vertical center of gravity as mechanically possible. In this way, the angular displacement between the axis of rotation of the rotary motor and the z-axis plane during a period of rocking following a translation movement is substantially eliminated. Practically speaking, the plane along which the translation forces are applied passes within 1 mm of the vertical center of gravity of the carriage. The axis of rotation of the rotary motor may hang somewhat below the plane upon which translation forces are applied.

Figure 2:
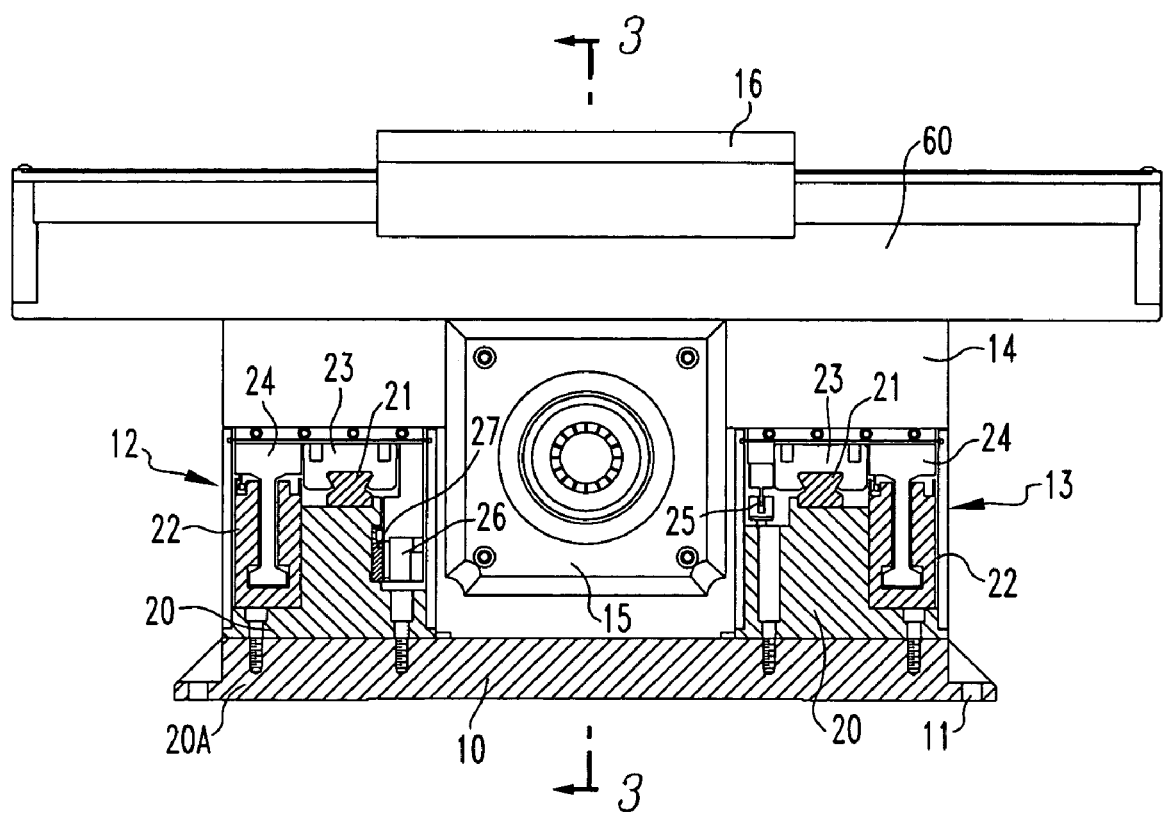
FIG. 2 is a section view along line 2—2 on FIG. 1 which is taken perpendicular to the theta-axis.

Referring to FIG. 2, the linear motors 12 and 13 are preferably permanent magnet linear motors, for example, direct drive brushless linear motors consisting of a noncontacting forcer coil 24 and a U-channel, rare-earth magnet track 22. This design eliminates backlash, windup, wear, and maintenance associated with ball screws. Motors of this type are available from, among others, Aerotech, Inc. of Pittsburgh, Pa. Other types of linear motors could be utilized as well.

Figure 3:
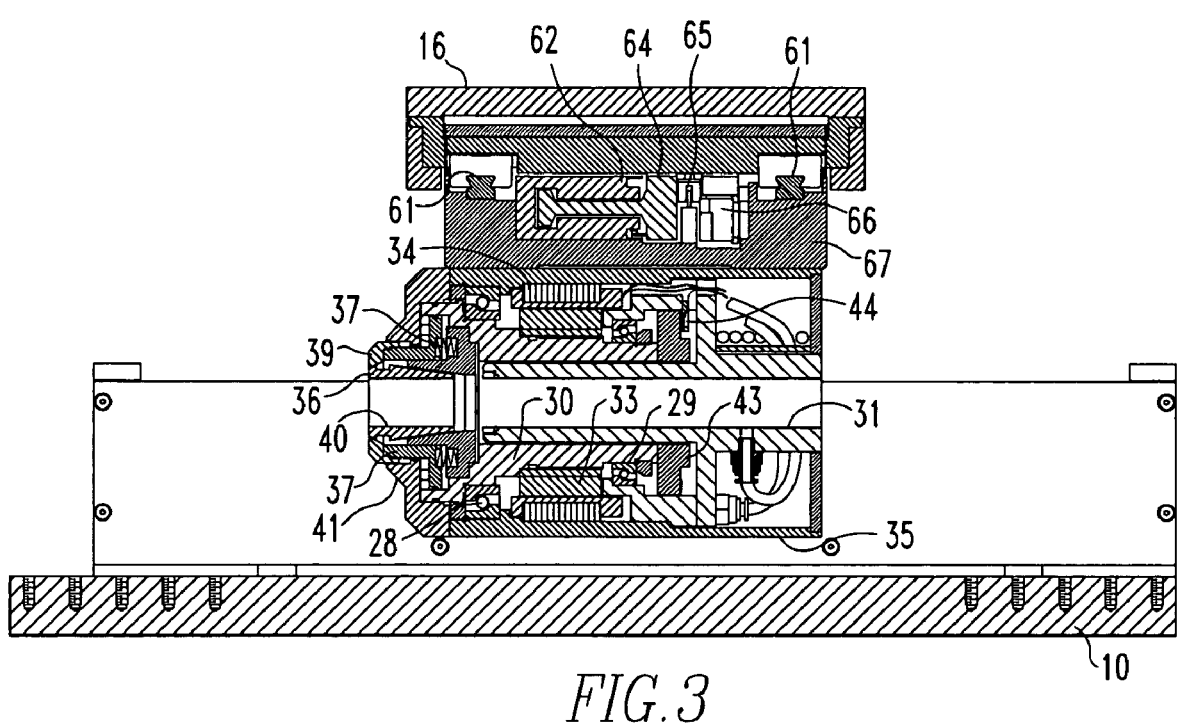
FIG. 3 is a section view along line 3—3 on FIG. 2 which is taken along the theta-axis.

Referring to FIG. 3, the rotary motor 15 is preferably a rotary brushless rare-earth magnet servomotor. It forms the basis of a direct drive theta-stage. Preferably, the rotating shaft has an axial bore and is provided with an air-operated collet chuck. A motor of this type is available from Aerotech, Inc. of Pittsburgh, Pa.

Referring now to FIG. 2, the linear motors 12, 13 are shown spaced apart, parallel, and positioned on the base plate 10. Associated with the motors are linear motion guides or bearings which may have, for example, cross roller bearings or air bearings. The rotary motor 15 is spaced with an equal distance between itself and the linear motors and with a rotating axis parallel to the linear motors.

Referring to FIG. 2, the linear motors are comprised of a linear spar 20 that is bolted to the base plate 10 by bolts 20A. The linear spar supports the track 21 of the linear bearing and the U-shaped magnet track 22. The magnet track 22 is a U-shaped channel fabricated from magnetic steel. It supports the rare-earth permanent magnets (not illustrated) arranged with alternating North and South poles facing inward at the forcer windings 24 along the length of the magnet track. The forcer windings 24 are comprised of nonmagnetic materials so as not to be attracted by the magnet track 22. Bearing trucks 23 ride on the tracks 21 of the linear bearings and support the first carriage 14. The forcer windings 24 are also secured to the first carriage 14. As shown in FIG. 2, the linear motor on the right side has a limit switch 25 associated therewith and the linear motor on the left side has an encoder read head 26 and encoder scale 27 associated therewith. As can be seen from FIG. 2, the linear motor applies translation forces to the carriage where the forcers are attached to the carriage.

Attached to the first carriage 14 and sliding over the linear motors 12, 13 is a flexible sliding cover. The cover slides over rollers not shown guided downward at each end of the linear motors.

Referring to FIG. 3, the rotary motor 15 carried by the first carriage 14 will now be described. Bearings 28 and 29 support rotating shaft 30 from an armature case 35 that is integral with the first carriage 14. Armature windings 34 are secured to the armature case 35 in a typical manner. The windings may be supported by a laminated magnetic core with slots for receiving the windings or the windings may not be supported by a core with slots (i.e., slotless). Permanent magnets 33 are secured to the outer cylindrical surface of the shaft 30 in a typical manner. A rotary encoder scale 43 is attached to the shaft. A rotary encoder read head 44 is attached to armature casing 35.

According to one particularly advantageous embodiment, the armature winding is slotless and the shaft is made of aluminum or another lightweight metal. While the torque/inertia ratio for this embodiment is low, the absence of cogging due to the slotless winding results in a superb theta-stage for the manufacture of stents.

The shaft has a bore 31 extending end to end. In a particularly advantageous embodiment, nested within the bore 31 is a water jacket assembly (not shown) for cooling the shaft and a workpiece held in the shaft.

The bore 31 of the shaft 30 stepwise widens at one end to form two cylindrical seats, one having a larger diameter than the other. A tapered collet chuck 36 is fixed in the cylindrical seat of lesser diameter. A piston 37 rides within the seat of larger diameter and is telescoped over the tapered collet chuck 36. The piston 37 is biased by a spring toward the tapered collet chuck. Threaded to the piston is an annular threaded retaining cap 39 that has a tapered inner rim. A collet 40 is positioned to slide within the tapered collet chuck 36 and is held in place by the tapered inner rim of the retaining cap 39. According to one preferred embodiment, the collet 40 is of the ER-16 series available in multiple sizes from 0.05 mm to 10 mm. An annular manifold 41 is secured to the armature case 35. A piston chamber is formed between the manifold 41, the piston 37, and the larger diameter seat. Seals are provided between the piston and the larger diameter seat, between the shaft and the manifold, and between the manifold and the piston, respectively. A passage (not shown) is in communication with the piston chamber and a fitting is provided on the outside of the manifold 41 for supplying pressurized air to the piston chamber to force the piston over the collet to tighten the collet onto a workpiece (not shown). In this embodiment, the air pressure engages the collet with the workpiece; however, the piston can be arranged such that air pressure would release the collet.

The base plate 10 may have at least one auxiliary tool (not shown) comprising support brackets guiding, grasping, and feeding a workpiece along the axis of the rotor.

The x-stage comprises a base 60 removably mounted to the first carriage. The base supports tracks 61 of linear bearings and U-shaped magnet track 62. The magnet track 62 is a channel fabricated from magnetic steel. It supports rare-earth permanent magnets (not illustrated) arranged with alternating North and South poles facing the forcer winding 64 along the length of the magnet track. The forcer winding 64 and magnet track 62 define a linear motor. In this embodiment, the forcer winding is comprised of nonmagnetic materials so as not to be attracted to the magnet track 62. Other types of linear motors could be also used. Bearing trucks 62 ride on tracks 61 of the linear bearings of the second carriage 16. The forcer winding 64 is secured to the second carriage. The x-axis limit switch 65, encoder read head 66, and encoder scale 67 are associated with the linear motor.

The linear motors and rotary motor have associated position feedback means. In the specific embodiment described herein, position feedback is supplied from encoders. However, other position feedback means include resolvers and laser interferometers.

Incremental encoders are commonly used measurement transducers. Optical incremental encoders pass light from a lamp or light-emitting diode at a grating attached to the axis to be measured. The grating normally has two tracks offset 90 degrees apart with respect to each other (in quadrature). A single marker on a third track serves as a home marker (in the case of a rotary encoder, a one-per-revolution marker). The light reflected from the grating continues through a reticule or mask which, together with the grating, acts as a shutter. The shuttered light falling on a detector results in the generation of electrical signals. These signals are amplified and output as two amplified sinusoidal or square waves in quadrature and are output on two separate channels as signals SIN and COS. With simple incremental encoders, the position is measured by counting the zero crossings (sinusoidal) or edges (square waves) of both channels. Where greater precision is required, the amplified sinusoidal signals (SIN and COS) are sent to an encoder multiplier where the intermediate positions are resolved at spaced time intervals.

An encoder multiplier uses the SIN and COS signals to resolve many positions within one grating period (scribe lines). The multiplier, for example, is able to produce up to 65,000 transitions within one grating period as opposed to the four by a simple incremental encoder. See, for example, U.S. Pat. No. 6,356,219 entitled "Calibrated Encoder Multiplier". Feedback from the incremental encoders can be used to control the currents applied to each phase of the windings to precisely position the stages.

Having thus defined our invention in the detail and particularity required by the Patent Laws, what is desired protected by Letters Patent is set forth in the following claims.

The invention claimed is:

1. A dual-function, three-axis positioning system having a first horizontal translation axis (z-axis) and a rotary axis (theta-axis) parallel with the translation axis and a second horizontal translation axis (x-axis) perpendicular to the first horizontal translation axis comprising:
  a base plate having upper surfaces lying in a plane;
  parallel spaced apart linear translation stages each having parallel linear bearings with bearing surfaces mounted at a substantially equal distance from the planar surfaces of the base plate, each linear translation stage having a brushless linear motor;
  a first carriage supported between the parallel translation stages by the linear bearings for translation along the first horizontal translation axis;
  a rotation stage carried by the first carriage between the parallel translation stages, said rotation stage comprising a brushless rotary motor having a shaft journaled with an axis parallel to the linear bearings for rotation about the rotary axis, the first carriage and rotation stage having a vertical and a horizontal center of gravity;
  a removable or permanently fixed linear translation stage comprising a second carriage and a base mounted to the first carriage, said removable or fixed linear translation stage supported by parallel linear bearings and a brushless linear motor between the base and the second carriage for translation along the second horizontal translation axis; and
  each brushless linear motor connected to the first carriage being connected to the first carriage to apply translation forces in a horizontal plane intersecting said vertical center of gravity if/or when the second carriage is removed.

2. The dual-function, three-axis positioning system according to claim 1, wherein a linear position feedback device is associated with one brushless linear motor.

3. The dual-function, three-axis positioning system according to claim 1, wherein a rotary feedback means is associated with the brushless rotary motor.

4. The dual-function, three-axis positioning system according to claim 1, having a fluid-actuated, workpiece-holding chuck or collet attached to the shaft of the rotary motor.

5. The dual-function, three-axis positioning system according to claim 1, wherein the shaft of the rotary motor is hollow to permit a cylindrical workpiece and/or a fluid cooling jacket to be positioned therein.

6. The dual-function, three-axis positioning system according claim 1, wherein the horizontal center of gravity of the carriage and rotary stage is halfway between each linear motor.

7. The dual-function, three-axis positioning system according to claim 1, wherein each linear stage contains a linear motion guide, cross roller bearing, or air bearing.

8. The dual-function, three-axis positioning system according to claim 1, wherein each linear motor is connected to the carriage at multiple locations spaced in the direction of linear translation.

* * * * *